US009333275B2

(12) United States Patent
Berentsveig

(10) Patent No.: US 9,333,275 B2
(45) Date of Patent: *May 10, 2016

(54) NEBULIZER MANIFOLD

(71) Applicant: Saban Ventures Pty Limited, Alexandria, New South Wales (AU)

(72) Inventor: Vladimir Berentsveig, Alexandria (AU)

(73) Assignee: SABAN VENTURES PTY LIMITED, New South Wales (AU)

( * ) Notice: Subject to any disclaimer, the term of this patent is extended or adjusted under 35 U.S.C. 154(b) by 95 days.

This patent is subject to a terminal disclaimer.

(21) Appl. No.: 14/150,398

(22) Filed: Jan. 8, 2014

(65) Prior Publication Data

US 2014/0120008 A1    May 1, 2014

Related U.S. Application Data

(62) Division of application No. 13/059,050, filed on May 3, 2011, now Pat. No. 8,668,882.

(30) Foreign Application Priority Data

Aug. 15, 2008    (AU) ................................ 2008904201

(51) Int. Cl.
*A61L 2/00*    (2006.01)
*A61L 9/00*    (2006.01)
(Continued)

(52) U.S. Cl.
CPC .. *A61L 2/22* (2013.01); *A61L 2/186* (2013.01); *A61L 2202/15* (2013.01); *A61L 2202/24* (2013.01)

(58) Field of Classification Search
CPC .................................... A61L 2/00; A61L 2/22
USPC ......... 422/1, 4, 22, 24, 28, 33, 121, 124, 186, 422/186.07, 186.3, 295, 298, 300, 302, 422/305–306
See application file for complete search history.

(56) References Cited

U.S. PATENT DOCUMENTS 5,527,516 A    6/1996    Yamamoto et al.
5,961,937 A    10/1999    Gobbato
(Continued)

FOREIGN PATENT DOCUMENTS

FR    2 744 041    8/1997
FR    2 825 636    12/2002
(Continued)

OTHER PUBLICATIONS

Supplementary European Search Report for EP Application 09 80 5240 dated Nov. 23, 2011 (6 pages).
(Continued)

*Primary Examiner* — Monzer R Chorbaji
(74) *Attorney, Agent, or Firm* — Finnegan, Henderson, Farabow, Garrett & Dunner, LLP

(57) ABSTRACT

A manifold which introduces sterilant aerosol to a sterilization chamber for the disinfection of an article. The manifold defines the terminal portion of a fluid pathway from an aerosol generator to the sterilization chamber and comprises at least one chamber inlet port for introducing aerosol into the sterilizing chamber. The manifold is configured to provide directional aerosol flow tangential to the surface of the article, which is preferably of a known configuration and maintained in a predetermined position with respect to the manifold, such that it does not receive a direct flow of aerosol from the manifold. Preferably, the manifold is U-shaped, or bifurcate and defines a plane and with a chamber inlet ports are directed away from that plane. The chamber inlet ports are preferably paired so they create a circular motion of aerosol that moves around the article. Also sterilization apparatus including the manifold.

10 Claims, 10 Drawing Sheets

(51) Int. Cl.
*A61L 2/22* (2006.01)
*A61L 2/18* (2006.01)

(56) References Cited

U.S. PATENT DOCUMENTS

| | | | |
|---|---|---|---|
| 6,162,395 A * | 12/2000 | Kowanko | 422/33 |
| 8,668,882 B2 * | 3/2014 | Berentsveig | 422/298 |
| 2008/0029133 A1 | 2/2008 | Kunkle | |

FOREIGN PATENT DOCUMENTS

| | | |
|---|---|---|
| GB | 2 217 250 | 10/1989 |
| RU | 2296585 C1 | 4/2007 |
| WO | WO 99/66961 | 12/1999 |
| WO | WO 2007/102798 | 9/2007 |

OTHER PUBLICATIONS

International Search Report from the Australian Patent Office for International Application No. PCT/AU2009/001046 (Mail date Sep. 9, 2009).

Office Action issued by the Chinese Patent Office dated Feb. 4, 2013 (7 pages).

\* cited by examiner

NEBULIZER MANIFOLD

This is a divisional application co-pending application Ser. No. 13/059,050, filed May 3, 2011, which is incorporated herein by reference.

TECHNICAL FIELD

The invention relates to manifolds for controlling the flow of an aerosol in a defined manner. The invention is described primarily with reference to the introduction of a sterilant aerosol into a closed sterilisation chamber for the purpose of sterilising medical articles such as ultrasonic probes, although it will be appreciated that it is not limited to such a use.

BACKGROUND ART

Any discussion of the prior art throughout the specification should in no way be considered as an admission that such prior art is widely known or forms part of common general knowledge in the field.

Sterilizers are used in the medical, food and packaging industries to kill and thereby prevent the transmission of transmissible agents such as spores, fungi, and bacteria. A typical sterilizer creates a set of physical conditions in a sterilisation chamber that effectively kills nearly all of these transmissible agents.

Contacting articles in need of sterilisation with sterilant aerosols is one known method of sterilisation. A conventional aerosol sterilisation apparatus has a sterilisation chamber with an aerosol inlet valve and an aerosol outlet valve, an aerosol generator (typically an ultrasonic nebulizer) in fluid communication with the chamber via the inlet valve and a fan upstream of, and in fluid communication with, the aerosol generator.

In use, an article requiring sterilisation is placed in the chamber, which is then sealed. The aerosol inlet valve is opened and the aerosol outlet valve is closed. The fan is engaged, which creates a gas stream through or the past the aerosol generator into the chamber. A passive vent in the sterilisation chamber allows for pressure equalization as required, to permit gas flow in and out of the sterilisation chamber. The aerosol generator, which contains the desired sterilant, is then activated, putting a large number of small sterilant droplets into gas stream. The droplets are carried by the gas stream to create an aerosol which travels into the sterilisation chamber. The sterilant concentration in the aerosol stream can be adjusted by changing either the flow rate of the gas stream, the productivity of the aerosol generator, or the concentration of the liquid sterilant used.

The passive waste vent allows some flow to pass through it, allowing the sterilisation chamber to remain at approximately room pressure. This passive system may include a pathway for flow to the outside air past catalytic elements that react with the sterilant and break the sterilant down into a safer chemistry suitable for disposal.

After a period of time, the fan and the aerosol generator are deactivated and the air inlet valve is closed, hence completing the sterilant delivery phase. The exit valve is then opened and aerosol is actively removed, typically by way of a pump that pulls aerosol and vapour out of the sterilisation chamber at a high rate. The removal system may include a pathway for flow between the sterilisation chamber and outside air past catalytic elements that react with the sterilant and break the sterilant down into a safer chemistry suitable for disposal. The passive vent allows a source of fresh air to be drawn into the sterilisation chamber from the outside air.

It is generally desirable for the total sterilisation cycle time to be as short as possible. Short reprocessing durations increases the number of times the sterilised article can be used in a given period, which in turn increases the number of patients per day that can be treated. In the case where the article to be sterilised is a high-cost medical device, short cycle times can generate significant financial savings for a health care provider.

One of the limitations of using an aerosol-based sterilizer is that in order to gain the required level of microbiological reduction in a short sterilisation time a high concentration (ie a high mist density) of aerosol sterilant is required. During sterilisation, a high concentration of aerosol sterilant causes droplets to coalesce on the surface of the article. This can be particularly prevalent at a location on the article that is subject to a direct mist stream from the chamber inlet. This can also lead to multilayer B.E.T.-like absorption on the surface of the sterilized article. Coalesced and absorbed droplets can be difficult to remove from the article at the end of the sterilisation process. Large levels of residual sterilant left on the sterilised article can be harmful to operators and patients and as such are undesirable in a fully automated sterilisation device.

While the residual sterilant may be removed by washing, this is an expensive feature to add to an automated sterilisation device, and requires sterile water and fresh water supplies that cannot always be easily obtained. Alternatively, it is also undesirable to have staff hand-washing articles, as this requires the use of safety apparatus which can be expensive (such as fume hoods), can take up valuable time and space and moreover increases the risk of harmful sterilant coming into contact with an operator or patient.

A washing phase also requires a subsequent drying phase which adds considerably to apparatus turn-around times.

In conventional sterilization apparatus, the aerosol is usually introduced into the sterilization chamber at a single point, via a single chamber inlet port. As a result, the distribution of the aerosol particles tends to fan out from that single point. More droplets contact the article to be sterilised at a point close to the aerosol inlet port, and contact the article at higher velocity, leading to splattering on the surface and the build up of condensate. Similarly, the areas of the article to be sterilised which are more remote from the aerosol inlet may receive a smaller dose of aerosol. In such cases, in order to ensure sterilization of the entire article, it becomes necessary to increase the total sterilant dose to compensate for areas of the article that may receive a smaller dose. Increasing sterilant dose may be achieved by increasing the length of time to carry out the sterilisation or by increasing the amount of sterilant delivered in a given time. Both methods can exacerbate the splattering and condensation effect in areas close to the single chamber inlet port.

One method to reduce the level of condensation and splattering near the inlet port is to move the article to be sterilized further away from the inlet port, allowing it to better disperse before contacting the article. However, greater distances require larger sterilization chambers, and this is undesirable for a number of reasons. Due to space limitations in many medical healthcare facilities, it is desirable for sterilisers to be as small as possible while still being capable of housing the article to be sterilized. Small sterilization chambers are also advantageous because they are both faster to fill with sterilant and faster to remediate than larger chambers. However, a small sterilization chamber increases the difficulty of introducing aerosol into the chamber while having it contact the article in an evenly-distributed fashion.

Maintaining an even mist distribution inside a sterilization chamber is important to ensure that there is even sterilization of the article to be sterilized. Once introduced into the sterilization chamber, aerosol droplets tend to fall due to gravity which results in a greater mist concentration at the bottom of the chamber than at the top of the chamber. In order to maintain an even distribution top to bottom, a high aerosol flow rate can be used to provide droplet lift. In this case the gas stream moves in an upward direction at a faster rate than droplets fall. A downside of using such a method is that the gas stream velocities used result in greater velocities for smaller droplets, and as there is typically a wide range of droplet sizes in an aerosol it is difficult to optimise such a system. Additionally, the smaller and higher-velocity droplets can collide with the article to coalesce on its surface, thus making removal of residual sterilant difficult.

Using a dense mist is desirable, as it provides fast sterilization, which in turn can enable short sterilization cycles. However, in practice, dense mists are susceptible to condensation. Prior art sterilizers often require noisy, large and expensive apparatus to remove condensation in a time-effective manner. Thus, in prior art sterilizers, in order to avoid condensation, the density of mist needs to be limited, meaning that short sterilization times cannot be realized.

Accordingly, there is a need to find improved methods of delivery of the aerosol to a sterilisation chamber, particularly a small chamber, so that the aerosol is delivered to the article to be sterilised in an even manner and at a relatively low velocity to minimise the possibility of condensation.

SUMMARY OF THE INVENTION

According to a first aspect the invention provides a manifold for introducing a sterilant aerosol to a sterilization chamber for the disinfection of an article, the manifold defining the terminal portion of a fluid pathway from an aerosol generator to the sterilization chamber; the manifold comprising at least one chamber inlet port for introducing aerosol into the sterilizing chamber and being configured to provide directional aerosol flow tangential to at least part of the surface of the article.

Preferably the manifold is configured to provide directional aerosol flow tangential to at least part of the surface of an article maintained in a predetermined position with respect to the manifold. It is also preferred that the manifold is configured to provide directional aerosol flow such that the article does not receive a direct flow of aerosol from the manifold. Preferably, the aerosol is directed not at the article.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

References to "sterilisation" and "disinfection" as used herein may be used interchangeably, and are also intended to include other levels of microbial reduction, to including but not limited to sterilisation, high and low level disinfection.

An aerosol is a large number of discrete particles suspended in a gas. When the gas is directed into a stream or jet, the particles are entrained in the gas and move in a generally cohesive manner about the mean path. However there will be a number of particles that follow pathways deviating from the mean path. The more significantly any given path deviates from the mean path, the smaller the number of particles that follow such a path. Additionally, the further that a group of aerosol particles travel from a common source, the more they disperse. Those skilled in the art will be well aware of such dispersive behaviour and will appreciate that in the present case, where a "direct", "directed", "tangential" or the like flow of an aerosol is disclosed, what is being referred to is the mean path taken by the droplets. In terms of the overall flow of aerosol under those circumstances, a skilled person will interpret terms such as "direct", "directed", "tangential" and the like as meaning "substantially direct", "substantially directed", "substantially tangential" and so on.

Preferably the article is of a predetermined shape.

Preferably each chamber inlet port includes a nozzle or duct to direct the aerosol flow. The manifold preferably comprises at least two chamber inlet ports, and more preferably at least four chamber inlet ports.

The manifold can be a continuous manifold, or can comprise a number of discrete sub-manifolds in fluid connection.

Preferably, the manifold defines a manifold plane and the chamber inlet ports are directed away from the manifold plane. In one embodiment, the manifold is a simple linear manifold that directs aerosol flow tangential to at least part of the surface of the article to be sterilized. In further embodiments, the manifold is in more than one plane and surrounds the article to be sterilised. The manifold can have any suitable configuration, with regard to the size and shape of the sterilizing chamber and/or the size, shape and nature of the article to be sterilized. In all cases though, the manifold has chamber inlet ports configured to direct aerosol flow tangential to at least part of the surface of the article to be sterilized.

More preferably the manifold is configured to distribute aerosol from around the article to be sterilized and tangential to at least part of the surface thereoff for example, via a U-shaped, square, circular or semi-circular, manifold.

Most preferably the manifold is U-shaped and defines a manifold plane and comprises diametrically opposed paired chamber inlet ports, such that a first port directs aerosol flow a first side of the manifold plane and a second port directs aerosol flow to a second side of the manifold plane.

Preferably the manifold comprises diametrically opposed paired chamber inlet ports, such that a first port directs aerosol flow to a first side of the manifold plane and a second port directs aerosol flow to a second side of the manifold plane.

In one preferred configuration the manifold is U shaped and preferably has two, three or four vertically spaced apart chamber inlet ports, along each arm. Alternatively, the manifold is bifurcate and preferably has two, three or four vertically spaced apart chamber inlet ports, along each arm. However, any number of chamber inlet ports may be present, depending upon the size of the chamber and the degree of aerosol particle size separation required.

The manifold can be formed from a single length of tubing. Alternatively, the manifold can be constructed such that is formed from two mated portions that have been engaged with each other to form a complete manifold. For example, the manifold may be formed from a channel which mates with a corresponding seal, such as when a channel in the body of a sterilizing chamber mates with a corresponding seal on the door of the sterilizing chamber, and where both come into engagement when the door of the sterilizing chamber is shut.

The manifold is preferably in the form of an elongate tub, and is more preferably of square cross section.

Preferably the manifold includes diametrically opposed paired chamber inlet ports which direct flow at a difference of angle of between 100 and 260 degrees. Preferably the diametrically opposed paired chamber inlet ports create a circular motion of aerosol in the chamber that moves around the article.

Preferably the minimum distance between the article to be sterilized and the manifold is less than 10 cm, more preferably less than 7 cm and even more preferably less than 5 cm.

Preferably the manifold inlet is located at the top of the manifold. In one particularly preferred configuration the manifold inlet is bifurcated and splits aerosol flow into the top of the two arms of the U shaped manifold.

According to a second aspect the invention provides sterilization apparatus including a manifold according to the preceding aspect, a sterilization chamber and detent means to maintain an article to be sterilized at a predetermined position in the chamber, whereby the aerosol flow is tangential to at least part of the surface of the article. Preferably, the manifold does not direct the aerosol at the article to be sterilized.

Preferably the sterilization chamber defines a chamber volume and aerosol is admitted to the chamber at a rate of between one and three times the chamber volume per minute.

The sterilization apparatus preferably further includes a passive vent. More preferably, there is at least one aerosol exit point positioned above the central vertical position of the chamber The sterilization chamber is preferably adapted to hold an ultrasound probe.

The article is preferably an ultrasound probe, in which case the sterilization apparatus also preferably comprises a collar to sealingly engage a portion of the article in the chamber and to restrain the predetermined article from contact with the chamber walls. The chamber is elongate with a collar at the top to hold the probe in such a way that the functional region of the probe is suspended substantially in the middle of the chamber, and so that the functional region of the probe is not in contact with the chamber walls. The manifold is located in a plane along the long axis of the ultrasound probe.

Preferably the chamber wall is heated. The manifold and chamber in combination are preferably configured to provide a vortexing aerosol flow. Preferably the article to be sterilized is at a point central to the vortexing aerosol flow.

DESCRIPTION

Figure 1:
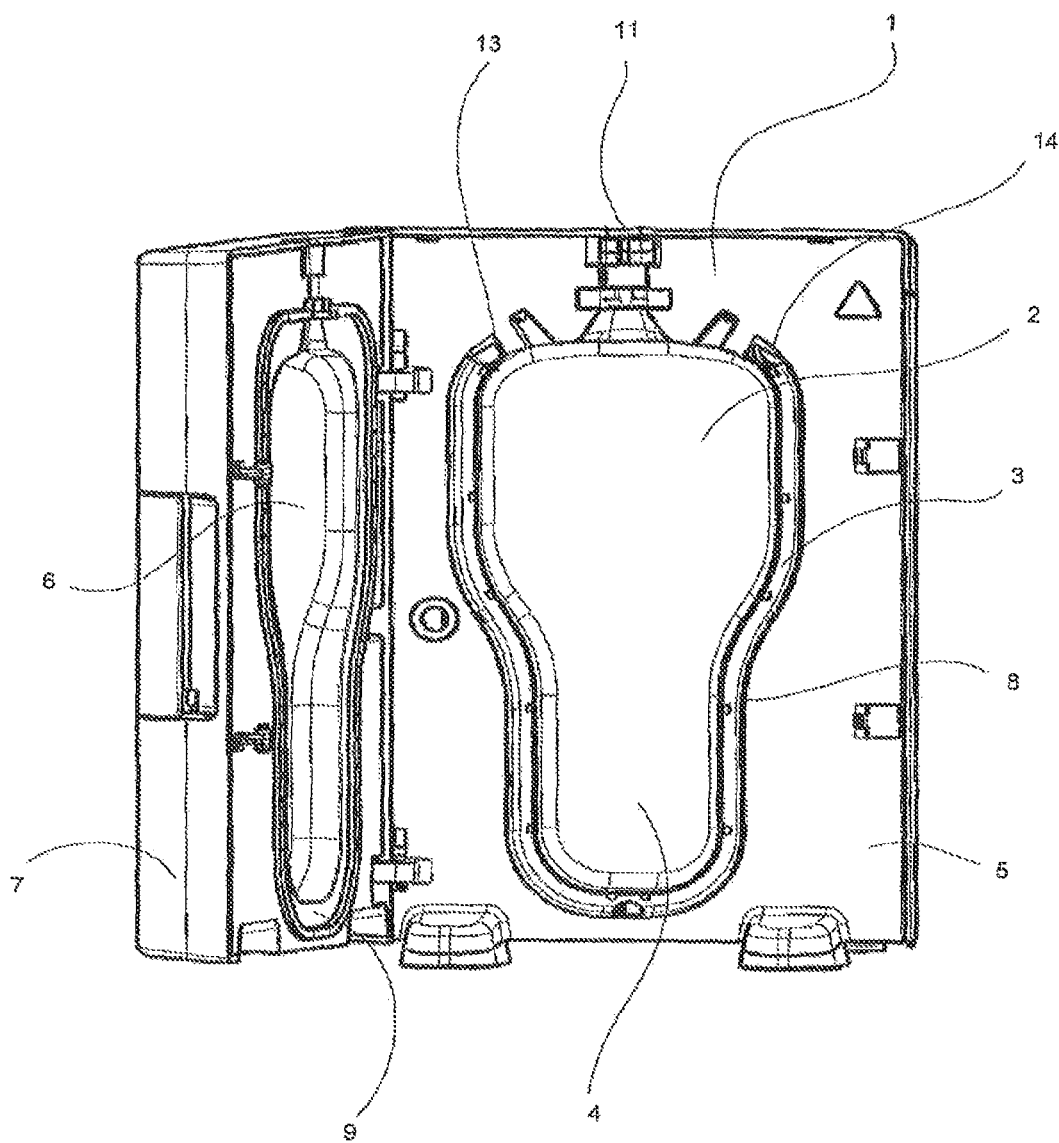
FIG. 1 shows a sterilization apparatus including a manifold of the present invention.

The present invention provides a means for creating and maintaining a dense and even mist distribution in a sterilization chamber that is marginally larger than the article (or articles) to be sterilized while greatly reducing condensation on the surface of the article.

These ends are met by directing aerosol tangential to the article to be sterilized. The tangential flow reduces the likelihood of condensation when high aerosol velocities are present by using droplet deflection. It has been observed that droplets are less likely to adhere to a surface if they contact it at a shallow angle compared to contacting an article in a perpendicular approach.

The manifold configuration of the present invention also provides a longer travel path for aerosol droplets, allowing aerosol to more fully disperse before coming into contact with the article, hence improving aerosol distribution in the sterilization chamber. The longer travel path provided allows aerosol to reduce in velocity before coming into contact with the article, hence reducing the likelihood of condensation.

The offset nature of the chamber inlet ports also allows them to be positioned very close to the article without the threat of condensation forming on the surface of the article, hence facilitating a smaller sterilization chamber.

By using multiple sterilant inlet ports, it is possible to more evenly control the distribution of aerosol in the sterilization chamber.

By controlling the flow rate of aerosol into the sterilization chamber, the aerosol can be maintained at approximately equal concentrations at across the vertical dimension of the chamber. An optimal flow rate is between one and three times the chamber volume per minute. Using higher flow rates may cause condensation on the surface of the article, and lower flow rates do not provide sufficient gas speed to allow droplets to overcome gravitational effects.

Preferably, the aerosol inlet ports are directed away from each other such that the direction of flow from each port pair varies by between 100 and 260 degrees. This provides an aerosol motion within the chamber that is directed around the article to be sterilized that is largely parallel or tangential to the surfaces on the device to be sterilized. The inlet ports need not be paired, ie on the same vertical plane, but can be offset vertically. The nozzles can also be placed so that they alternate in respect of which side of the article they are directed towards.

The tangential flow can also be achieved by having the manifold or manifolds offset from the central axis of the chamber.

Additionally, this tangential motion provides a means for separating larger droplets from smaller droplets. Larger droplets have higher linear momentum and are more likely to collide with the heated chamber wall, rather than be carried around inwards with the gas flow toward the article to be sterilised. This reduces the possibility of large droplets colliding with and condensing on the article. Providing a largely smooth chamber shape can help facilitate the vortex action (i.e. by rounding the corners of the chamber to prevent the disruption of the vortex). Thus, vortex droplet separation can be achieved.

It is possible to heating the chamber walls to between 40 and 80 degrees Celsius in order to rapidly evaporate off any droplets that may have condensed on the chamber walls due to the separation process, hence reducing the likelihood of a person coming into contact with condensed sterilant at any stage.

It is believed to be particularly advantageous to have the combination of vortex droplet separation and heated chamber walls. The larger droplets contact the chamber walls and evaporate, hence removing residual droplets from the chamber wall, reducing the chance that the operator could come into contact with harmful sterilant.

The invention will now be described with reference to the drawings.

FIG. 1 shows a steriliser 1 which has a sterilising chamber 2 which incorporates the nebuliser manifold 3. The chamber comprises a rear portion 4, which is housed in the body of the sterilizer 5. The chamber also has a front portion 6, in a mateable arrangement with the body. Closing the door 7 brings the front and rear portions of the chamber together.

Closing the door causes the chamber front to mate with the chamber rear to seal the sterilization chamber.

Figure 2:
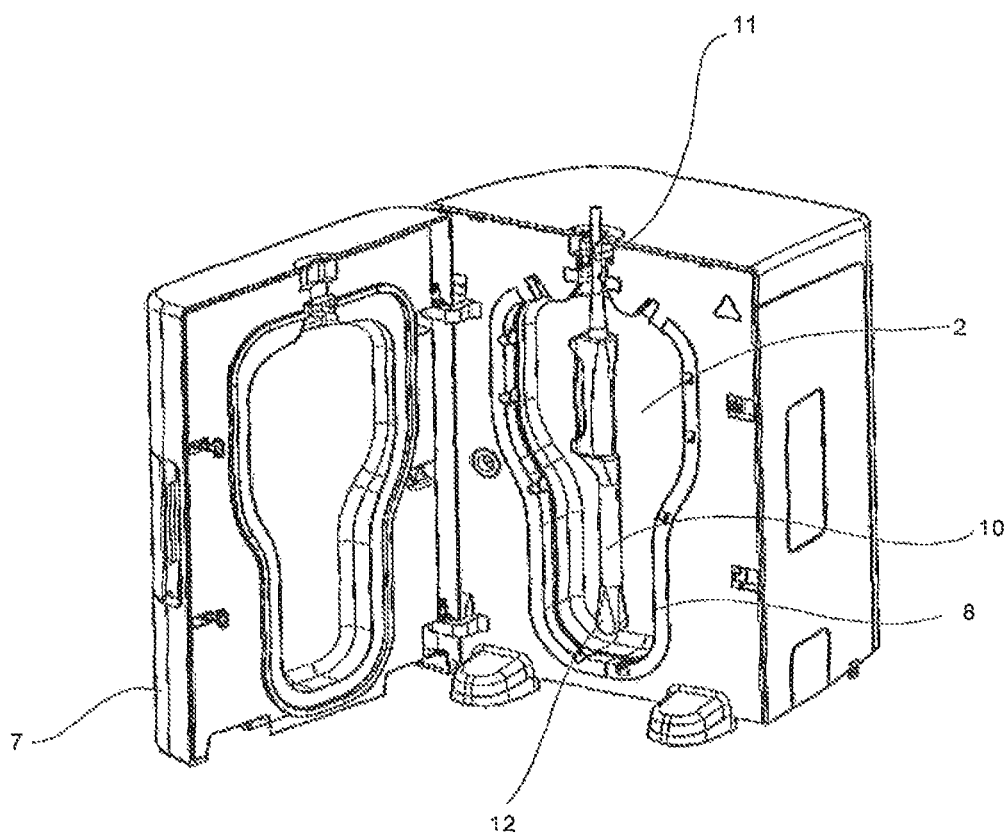
FIG. 2 shows a sterilization apparatus including a manifold of the present invention, in which is placed an ultrasonic probe for sterilization.

Turning to FIG. 2, the sterilising chamber 2 is adapted to receive an elongate probe, for example, an ultrasound probe 10, that is inserted into the open chamber, and held in a sealingly engaged manner by means of a collar 11, such that the head of the probe 12 is not in contact with any surface. When the chamber door 7 is closed and ultrasonic probe 10 is in place, a sealed chamber results which has the probe 10 suspended inside. The work surfaces of the probe are thus not in contact with any surface.

Whilst collar 11 is shown as detent means for positioning the article to receive a tangential flow, any suitable means such as brackets, mounting pins, clips etc may be used to maintain the article (such as an ultrasound probe) in a position where it will receive only a tangential aerosol flow, not a direct aerosol flow from the manifold. That is, the manifold directs the aerosol to the void space around the article, and not at the article itself. Preferably the article is suspended in the chamber, which is as small as possible with regards to the article to be sterilized—for example it is preferred if the distance between probe 10 and chamber wall 2 or manifold 8 is less than a few centimeters.

Figure 3:
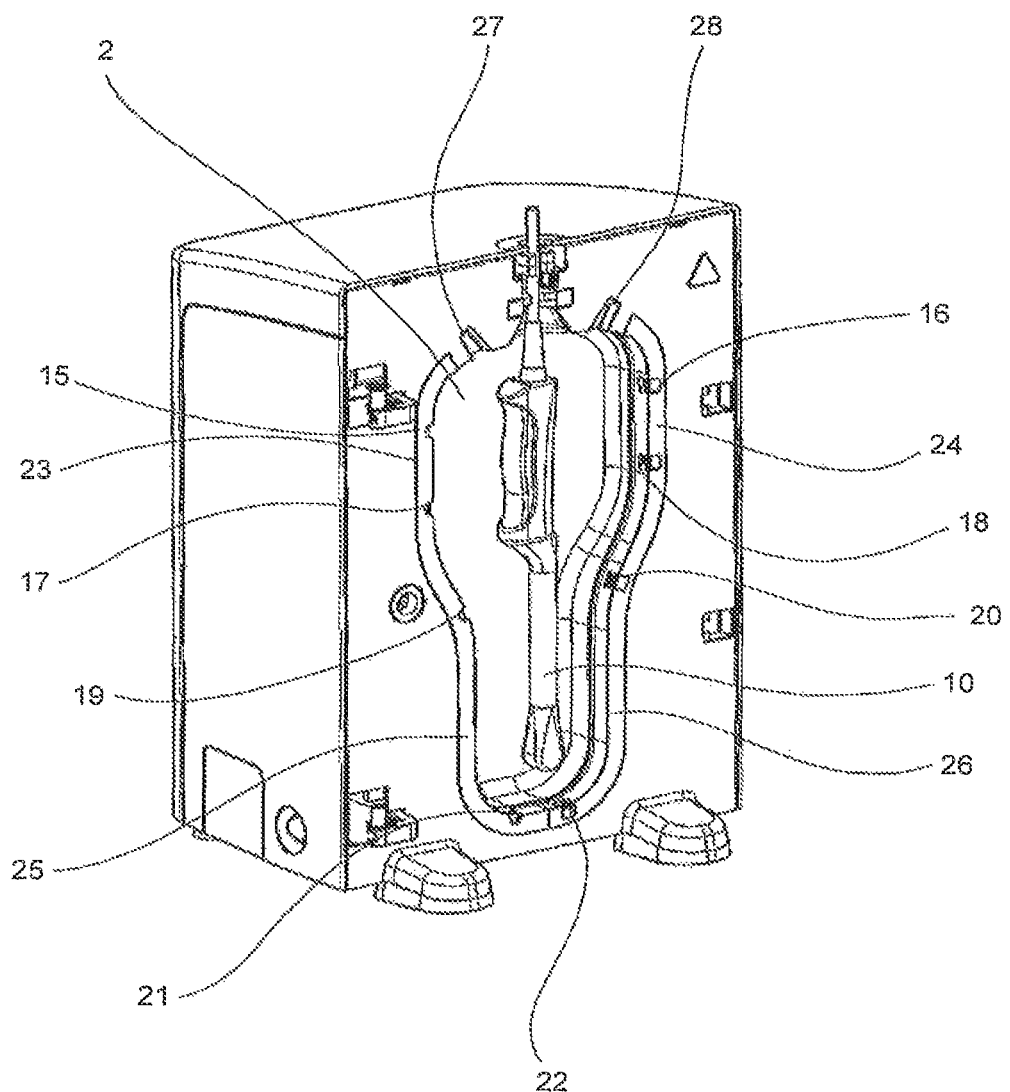
FIG. 3 is a closer view of FIG. 2, with the sterilization apparatus door removed for clarity.

FIG. 3 shows the sterilizer with the door 7 removed. The sealed sterilising chamber 2 is heated prior to use, along with the manifold 8. A fan not shown, in fluid connection with the manifold inlet ports 13 and 14 (see FIG. 1), is then started. The air flows into the manifold via inlet ports 13 and 14, and into the manifold. The air flow exits the manifold by the chamber inlet ports 15, 16, 17, 18, 19, 20, 21 and 22, and enters the sterilization chamber. The manifold 8 is a continuous tubular tube, of square cross section as shown, although it can be of any cross section, with a number of ports for introducing sterilising agent to the chamber. The manifold is substantially U shaped, with the upper portion of the parallel arms 23 and 24 being stepped apart further than the lower portion of the parallel arms 25 and 26.

Once the desired flow conditions are achieved, the ultrasonic nebulizer (not shown), which is in-line between the fan and the sterilization chamber 2, is activated. A sterilant liquid, most typically hydrogen peroxide, is supplied to the nebuliser and is nebulised. The aerosol exits the nebuliser and joins the air flow. The aerosol is then moved via the same path as the air flow, preferably a short path, to the manifold inlet ports 13 and 14 at the top of the manifold. Because the aerosol is under positive pressure, caused by the fan, and because the chamber has a passive exit vents 27 and 28 to allow the air pressure to be equalised, the nebulant flows through the manifold 8, out of the chamber inlet ports 15, 16, 17, 18, 19, 20, 21 and 22 and into the sterilization chamber 2.

A typical nebulant mist as produced in the nebulizer contains a distribution of aerosol particle sizes. Although the average particle size or MMAD, (Mass Median Aerodynamic Diameter) can be controlled, and the spread of particle sizes can be reduced by varying the nebulization conditions, the particles themselves are inevitably spread over a range of sizes.

Manifold 8 is preferably heated at a temperature sufficient to cause evaporation from the droplets, the aerosol particles become somewhat smaller as they transit through the manifold 8. Those particles that exit the manifold through the first chamber inlet ports 15 and 16, closest the manifold inlet, have a MMAD which is not significantly smaller than that which enters the manifold through manifold inlets 13 and 14. However, the particles that exit the manifold at the chamber inlet ports 21 and 22 distal to the manifold inlet have spent a longer time in the manifold 8 and there has been evaporation and a consequent reduction in particle size. As a result, the MMAD of these particles is reduced relative to its initial size. This will apply regardless of the initial size of the particles.

Thus, as the chamber inlet ports are moved further away from the manifold inlet, the droplet size issuing from that inlet port decreases. That is the aerosol particle size at outlet 21, 22<the aerosol particle size at outlet 19, 20<the aerosol particle size at outlet 17, 18<the aerosol particle size at outlet 15, 16.

The temperature of the droplets as they exit the manifold increases as a function of the amount of time spent in the manifold. For example, the droplets entering chamber 2 through chamber inlets 21 and 22 are not only smaller than the droplets exiting through chamber inlets 15 and 16, they are also at a higher temperature.

The resultant small droplets tend to move upwards, especially as a result of the air flow towards passive outlet vents 27 and 28 at the top of the chamber. However, the device still operates viably if the passive vent is located elsewhere in the chamber, including at the bottom of the sterilization chamber 2.

Thus, in the present invention the velocity of the aerosol droplets in the chamber is rather low. This is advantageous, since high velocity droplets tend to splatter on the surface, leading in some cases to an uneven build up of sterilant. A large build up of droplets is problematical as it means that either longer drying time is required to dry the article, or that there is an increased risk of residual material being left on the article. Residual sterilant, such as peroxide, can be injurious to users or patients.

Figure 4:
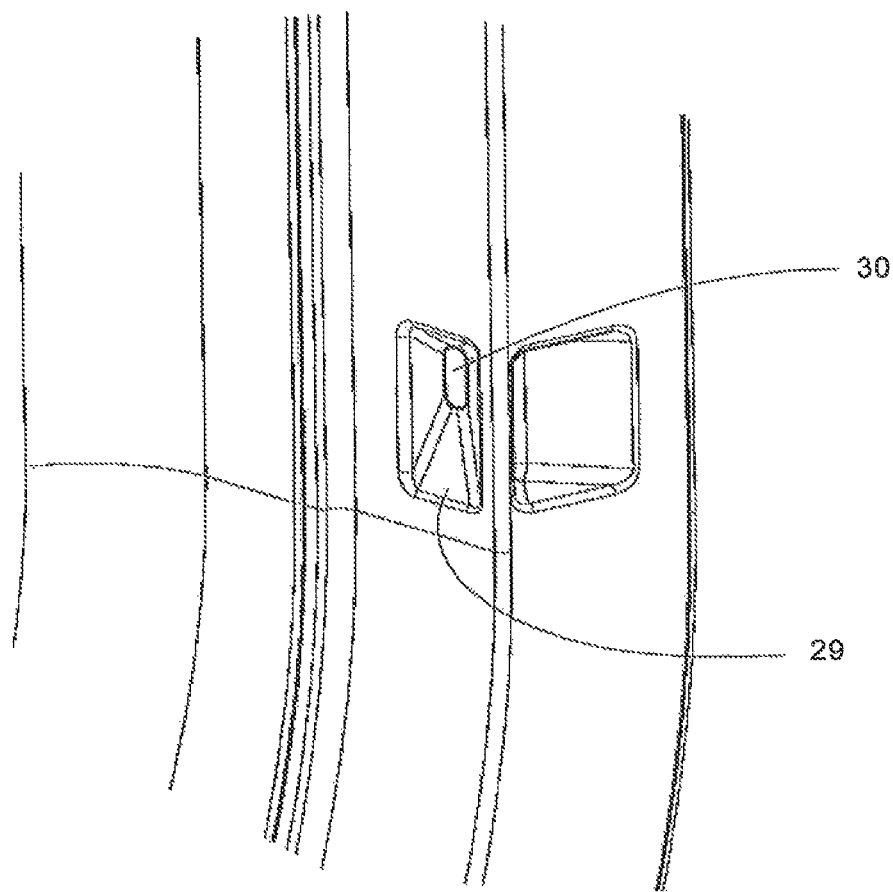
FIG. 4 is a close up view of the chamber inlet located on the manifold.
Figure 5:
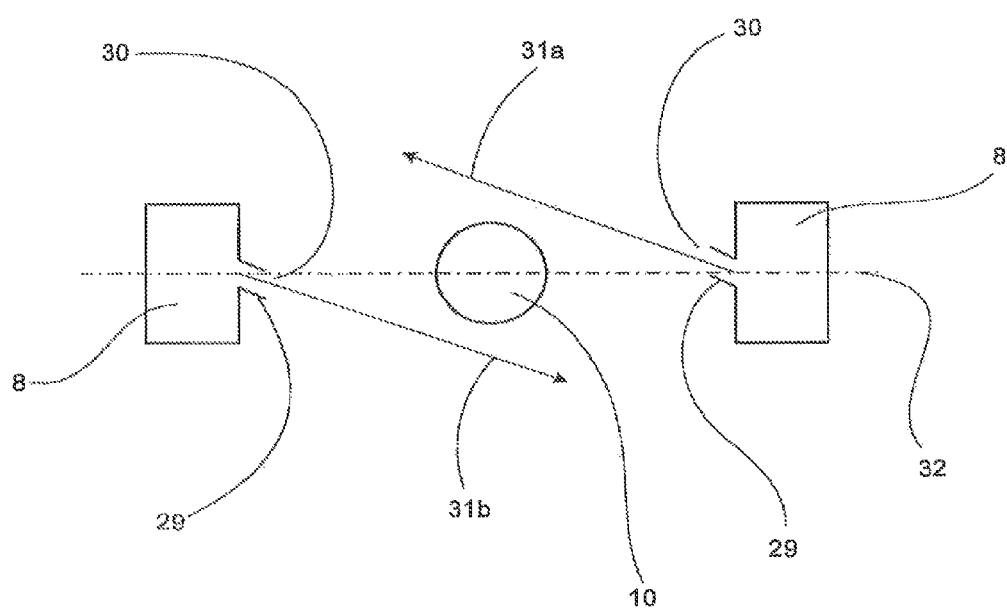
FIG. 5 is a cross sectional view of the gas flow from the manifold.

To further reduce the velocity of the droplets, the chamber inlet ports as shown in FIG. 4 are in the form of ducts 29 (or nozzles) having an off centre orifice 30 which leads to the aerosol being directed away from the object to be sterilised. In the present invention, the aerosol is directed to the side of the ultrasound probe. This is shown in FIG. 5, which is a horizontal cross section through the chamber. The gas flow 31a and 31b is to either side of the plane 32 defined by the manifold 8. The nozzles 29 and outlets 30 cause the flow to be away from plane 32 at an angle such that the probe 10 is contacted only at a shallow or tangential angle.

Figure 6:
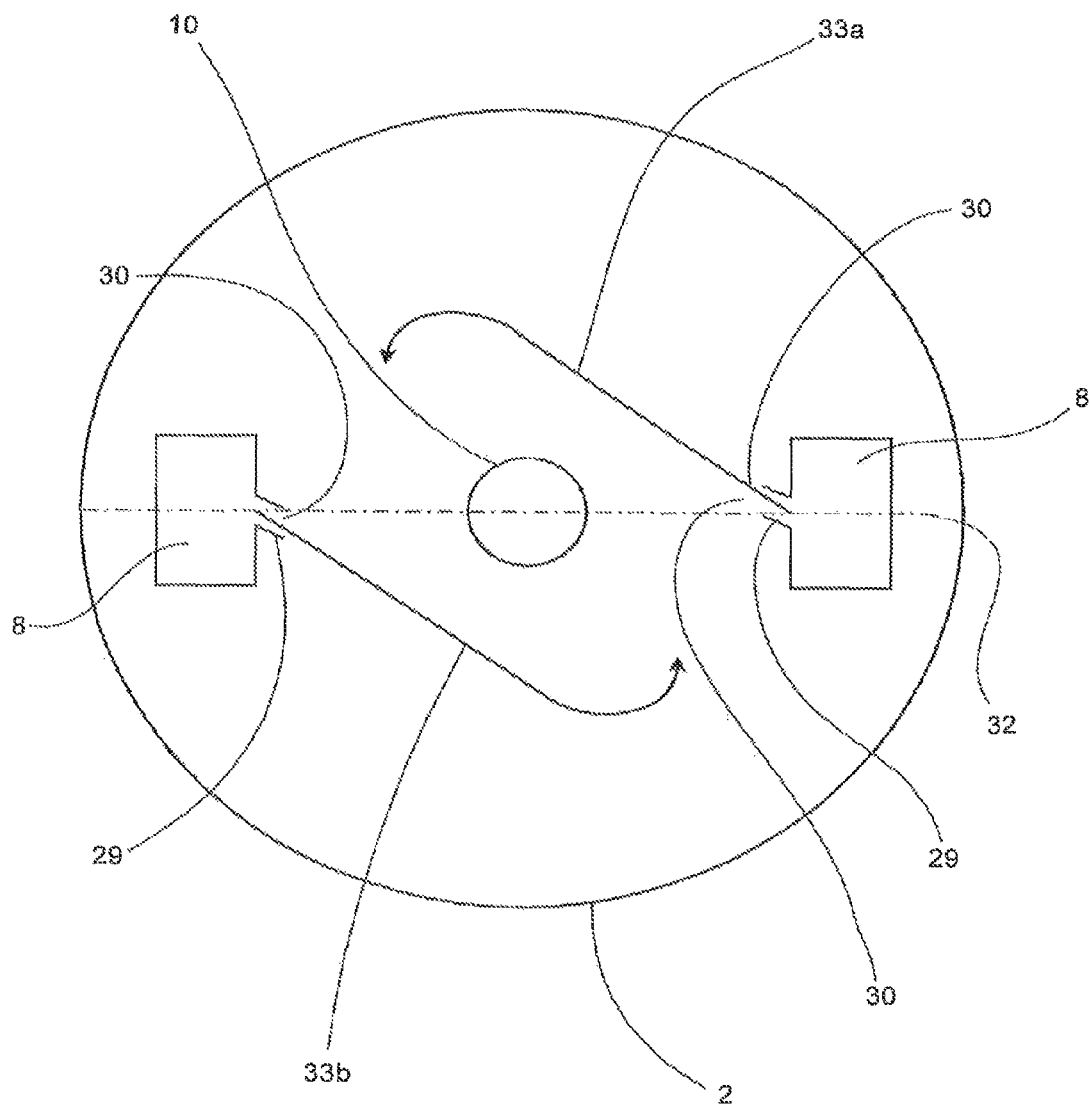
FIG. 6 is a cross sectional view of the gas flow from the manifold in a chamber of substantially circular cross section.

FIG. 6 shows the arrangement in a chamber 2 of substantially circular cross section. The chamber wall 2 causes the gas flows 33a and 33b to begin to circulate in a smooth manner near the chamber wall. The droplets are thus aimed at the void space in the chamber 2 around the sides of probe 10, rather than being directed at the probe itself. The droplets thus enter the chamber 2 at velocity, but because of the longer path available to the droplets they have the opportunity to slow and then diffuse around the chamber (downwards for large droplets, upwards for small droplets) until they contacting the probe 10 at low velocity. Larger droplets will be more inclined to take a more linear path, with less inward vortexing. Accordingly, larger particles will take a path that leads them into contact with chamber wall 2, which is heated and thus causes the larger droplets to evaporate.

FIGS. 5 and 6 have the chamber enlarged and simplified for clarity. In actuality, the chamber 2 is preferably conformed as closely as possible to the shape of the article. Whilst sufficient space needs to be present in the chamber to allow the mist to lose velocity, the chamber is otherwise sized as small as practicable.

Figure 7:
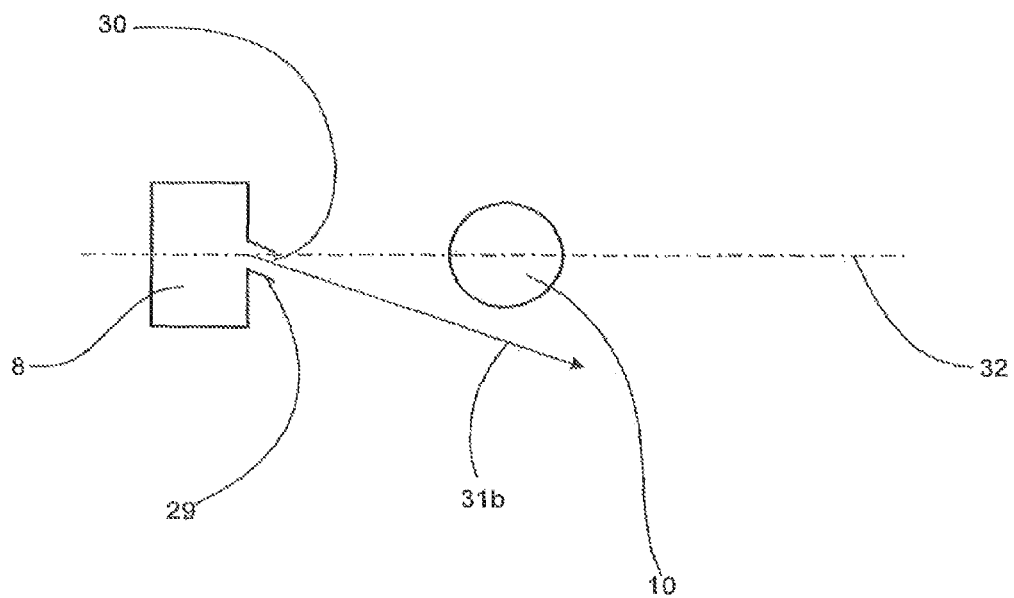
FIG. 7 is a cross sectional view of the gas flow from a single sided manifold.

FIG. 7 shows a horizontal cross section of a manifold arrangement where the aerosol is introduced from one side only. The gas flow 31b is directed to one side of the plane 32 defined by the manifold 8. The nozzles 29 and outlets 30 cause the flow to be away from plane 32 at an angle such that the probe 10 is contacted only at a shallow or tangential angle.

Figure 8:
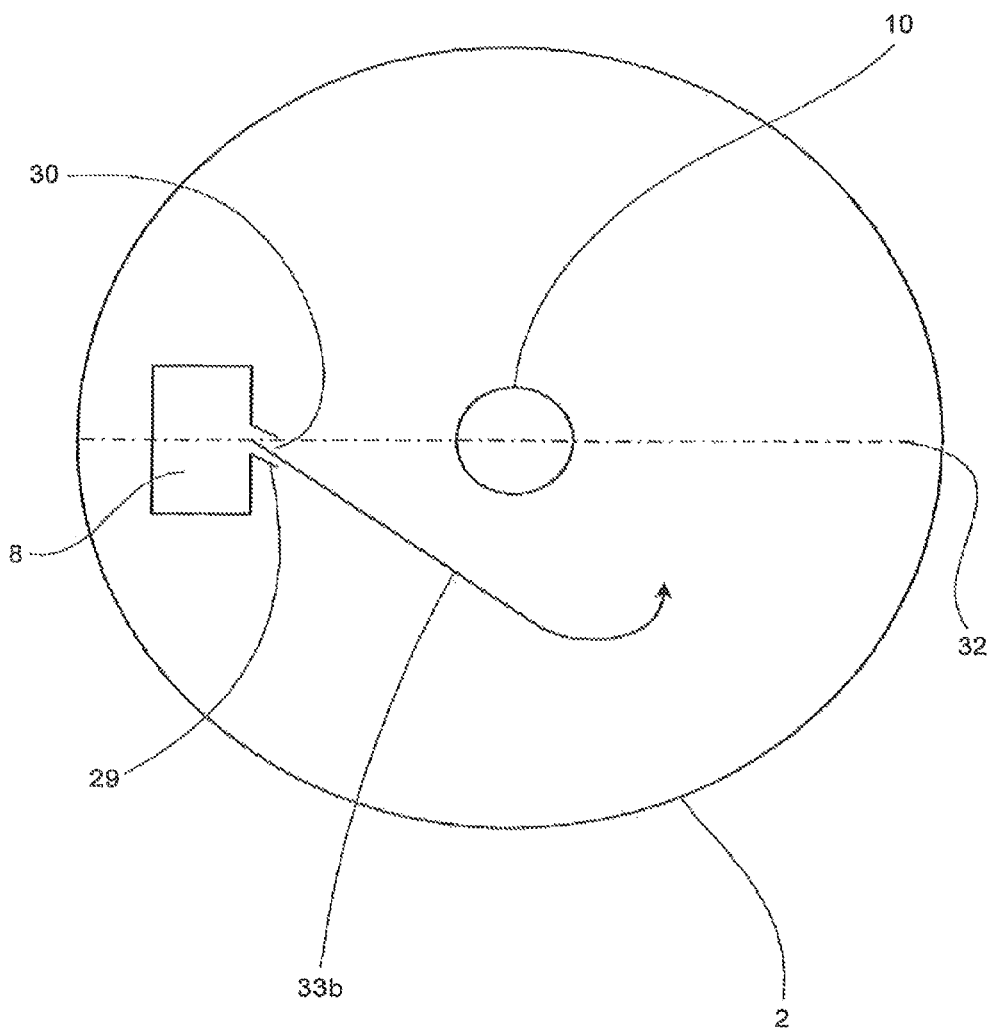
FIG. 8 is a cross sectional view of the gas flow from a single sided manifold in a chamber of substantially circular cross section.

FIG. 8 shows an arrangement similar to FIG. 6, but where the manifold is configured along one side of the chamber only. A single chamber inlet port can be used as shown, configured in such a way that the flow is tangential to the surface of an object (usually an object of a known predetermined shape) in the chamber. A single chamber inlet port is sufficient to create a vortexing flow. The chamber wall 2 still directs gas flow 33b to begin circulating in a smooth manner near the chamber wall. The droplets are thus aimed at the void space in the chamber 2 around the sides of probe 10, rather than being directed at the probe itself. The droplets thus enter the chamber 2 at velocity, but because of the longer path available to the droplets they have the opportunity to slow and then diffuse around the chamber (downwards for large droplets, upwards for small droplets) until they contact the probe 10 at low velocity.

Figure 9:
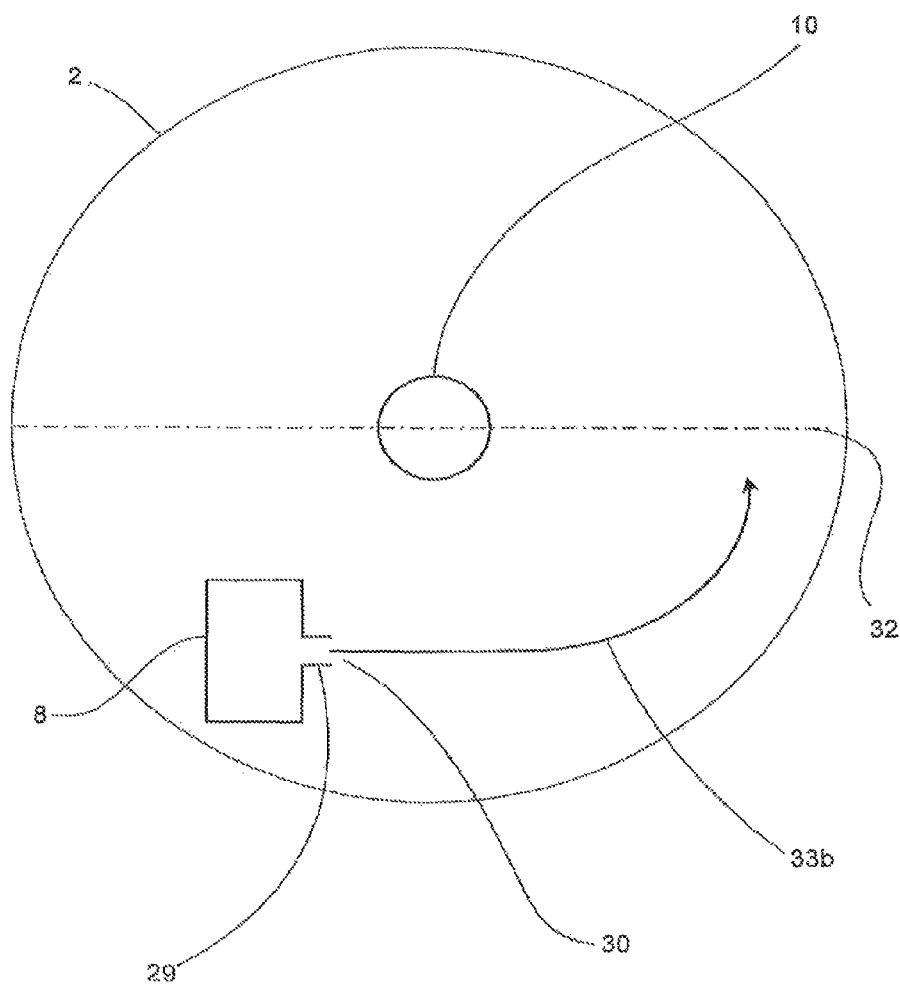
FIG. 9 is a cross sectional view of the gas flow from an offset manifold in a chamber of substantially circular cross section.

The tangential flow can also be achieved by having the manifold or manifolds offset from the central axis of the chamber. FIG. 9 shows how a manifold 8 may be positioned offset from the axis 32. In such a case, it is not necessary to have duct 29 direct flow away from the article. It can be seen that this configuration maintains flow 33b tangential to the article, while still providing vortex separation.

Figure 10:
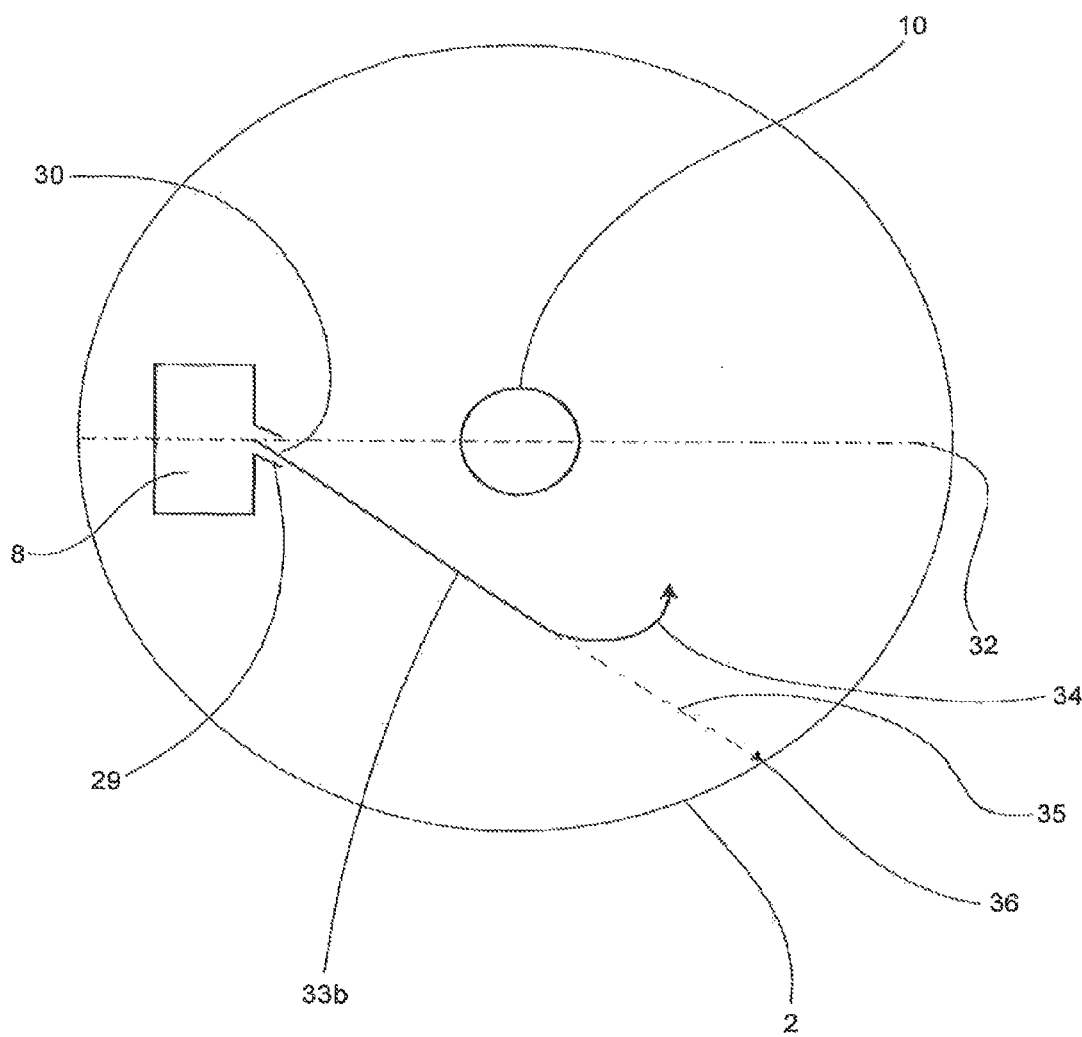
FIG. 10 is a cross sectional view of the gas flow from a single sided manifold in a chamber of substantially circular cross section, showing vortex separation of aerosol droplets on the basis of momentum.

FIG. 10 shows a similar configuration to FIG. 8, but illustrates in a simplified form the different paths taken by varying sized droplets. Smaller droplets follow the gas flow around the chamber, as shown by path 34. Larger droplets have a higher linear momentum than smaller droplets as they exit from manifold 8. The largest droplets will have the most linear path 35, which leads them to collide with chamber wall 2 at point 36. Because the chamber is heated, the larger droplets evaporate. Thus, the vortexing is a means of separating and selectively removing larger droplets from the chamber. A more even, dense mist of smaller droplets is thus available for sterilization.

The claims defining the invention are as follows:

1. Sterilization apparatus including:
   a sterilization chamber;
   detent means to maintain an article to be sterilized at a predetermined position in the chamber; and
   a manifold for introducing a sterilant aerosol to the sterilization chamber for the disinfection of an article, the manifold defining the terminal portion of a fluid pathway from an aerosol generator to the sterilization chamber, the manifold defining, a manifold plane, said manifold comprising at least one chamber inlet port directed away from the manifold plane for introducing aerosol into the sterilizing chamber and being configured to provide directional aerosol flow tangential to at least part of the surface of the article; wherein the manifold is configured to provide direction aerosol flow such that the article does not receive a direct flow of aerosol from the manifold.

2. Sterilization apparatus according to claim 1, further including a passive vent.

3. Sterilization apparatus according to claim 1, wherein there is at least one aerosol exit point position above the central vertical position of the chamber.

4. Sterilization apparatus according to claim 1, wherein the detent means comprises a collar to sealingly engage a portion of the article in the chamber and to restrain the article from contact with the chamber walls.

5. Sterilization apparatus according to claim 1, wherein a chamber wall is heated.

6. Sterilization apparatus according to claim 1, wherein the manifold and chamber in combination are configured to provide a vortexing aerosol flow.

7. Sterilization apparatus according to claim 6, wherein the article to be sterilized is at a point central to the vortexing aerosol flow.

8. A sterilization apparatus, comprising:
   a sterilization chamber;
   detent means to maintain an article to be sterilized at a predetermined position in the chamber;
   a passive vent connected to the sterilization chamber; and
   a manifold for introducing a sterilant aerosol to the sterilization chamber for the disinfection of an article, the manifold defining the terminal portion of a fluid pathway from an aerosol generator to the sterilization chamber, said manifold comprising at least one chamber inlet port for introducing aerosol into the sterilizing chamber and being configured to provide directional aerosol flow tangential to at least part of the surface of the article, wherein the manifold is configured to provide direction aerosol flow such that the article does not receive a direct flow of aerosol from the manifold.

9. A sterilization apparatus, comprising:
   a sterilization chamber, wherein a chamber wall is heated to a temperature sufficient to evaporate a sterilant aerosol;
   detent means to maintain an article to be sterilized at a predetermined position in the chamber; and
   a manifold for introducing the sterilant aerosol to the sterilization chamber for the disinfection of an article, the manifold defining the terminal portion of a fluid pathway from an aerosol generator to the sterilization chamber, said manifold comprising at least one chamber inlet port for introducing aerosol into the sterilizing chamber and being configured to provide directional aerosol flow tangential to at least part of the surface of the article, wherein the manifold is configured to provide direction aerosol flow such that the article does not receive a direct flow of aerosol from the manifold.

10. A manifold for introducing a sterilant aerosol to a sterilization chamber for the disinfection of an article maintained at a predetermined position in the chamber, the manifold defining the terminal portion of a fluid pathway from an aerosol generator to the sterilization chamber, the manifold defining a manifold plane; said manifold comprising at least one chamber inlet port directed away from the manifold plane for introducing aerosol into the sterilizing chamber and being configured to provide directional aerosol flow tangential to at least part of the surface of the article, wherein the manifold is configured to provide direction aerosol flow such that the article does not receive a direct flow of aerosol from the manifold.

* * * * *